United States Patent
Honda et al.

(10) Patent No.: US 9,974,934 B2
(45) Date of Patent: May 22, 2018

(54) SHEET PASTING DEVICE

(71) Applicant: OLYMPUS CORPORATION, Tokyo (JP)

(72) Inventors: Jun Honda, Fussa (JP); Masaki Hayashi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 625 days.

(21) Appl. No.: 14/633,236

(22) Filed: Feb. 27, 2015

(65) Prior Publication Data

US 2015/0165181 A1 Jun. 18, 2015

Related U.S. Application Data

(63) Continuation of application No. PCT/JP2013/073063, filed on Aug. 28, 2013.

(30) Foreign Application Priority Data

Aug. 30, 2012 (JP) ................................ 2012-190434

(51) Int. Cl.
*A61M 35/00* (2006.01)
*A61M 31/00* (2006.01)

(52) U.S. Cl.
CPC .......... *A61M 35/003* (2013.01); *A61M 31/00* (2013.01)

(58) Field of Classification Search
CPC ................. A61M 5/001; A61M 5/008; A61M 2025/0087; A61M 37/0015; A61M 2037/0023; A61M 2037/0046; A61M 31/00; A61M 35/003

See application file for complete search history.

(56) References Cited

U.S. PATENT DOCUMENTS 3,314,119 A * 4/1967 Hill .................... A47G 27/0462
16/16
4,043,338 A 8/1977 Homm et al.
4,169,303 A * 10/1979 Lemelson .......... A44B 18/0061
24/446

(Continued)

FOREIGN PATENT DOCUMENTS

JP H06-075508 U 10/1994
JP 9-501065 A 2/1997

(Continued)

OTHER PUBLICATIONS

Extended Supplementary European Search Report dated Apr. 26, 2016 in related European Application No. 13 83 3283.8.

(Continued)

*Primary Examiner* — Quynh-Nhu H Vu
(74) *Attorney, Agent, or Firm* — Scully, Scott, Murphy & Presser, P.C.

(57) ABSTRACT

A sheet pasting device including: an elastically-deformable sheet support section that is provided with a flat surface, and supports a sheet-shaped substance in a state in which the sheet-shaped substance is pasted to the surface; an extrusion member that is provided so as to be able to protrude from and retract into the surface of the sheet support section; and a drive mechanism that causes the extrusion member to protrude from and retract into the surface.

11 Claims, 12 Drawing Sheets

(56) References Cited

U.S. PATENT DOCUMENTS

| | | | | |
|---|---|---|---|---|
| 5,254,127 A * | 10/1993 | Wholey | ................ | A61B 17/11 285/397 |
| 5,383,897 A * | 1/1995 | Wholey | ............ | A61B 17/0057 606/213 |
| 5,693,029 A * | 12/1997 | Leonhardt | ......... | A61M 25/0084 604/264 |
| 5,728,150 A * | 3/1998 | McDonald | ................ | A61F 2/07 623/1.15 |
| 2002/0151866 A1 * | 10/2002 | Lundkvist | .............. | A61N 1/306 604/506 |
| 2006/0018701 A1 * | 1/2006 | Mohiuddin | ......... | A61M 35/003 401/132 |
| 2008/0294093 A1 * | 11/2008 | Maeda | ............... | A61B 17/3468 604/60 |
| 2009/0304753 A1 * | 12/2009 | Tsabari | .................. | A61J 3/071 424/400 |

FOREIGN PATENT DOCUMENTS

| | | |
|---|---|---|
| JP | 2007-229250 A | 9/2007 |
| JP | 2007-275236 A | 10/2007 |
| JP | 2008-173333 A | 7/2008 |
| JP | 2009-000511 A | 1/2009 |
| JP | 2011-147663 A | 8/2011 |
| WO | 2007/103264 A2 | 9/2007 |

OTHER PUBLICATIONS

International Search Report dated Dec. 3, 2013 issued in PCT/JP2013/073063.

* cited by examiner

SHEET PASTING DEVICE

CROSS-REFERENCE TO RELATED APPLICATIONS

This application is a Continuation Application of International Application PCT/JP2013/073063 filed on Aug. 28, 2013, which claims priority to Japanese Application No. 2012-190434 filed on Aug. 30, 2012.

The Contents of International Application PCT/JP2013/073063 and Japanese application No. 2012-190434 are hereby incorporated by reference herein in its entirety.

TECHNICAL FIELD

The present invention relates to a sheet pasting device.

BACKGROUND ART

Conventionally, there has been known a delivery and administration instrument for therapeutic substances that delivers a sheet-shaped therapeutic substance into a body, and pastes the sheet-shaped therapeutic substance to a diseased site (e.g., see Patent Literature 1.).

The instrument delivers the sheet-shaped therapeutic substance by placing the therapeutic substance on a flat sheet support section such that a plurality of opening portions provided in the sheet support section are closed by the sheet-shaped therapeutic substance, decreasing the pressure of a fluid fed to the opening portions, and thereby causing the therapeutic substance to adhere to the sheet support section. The instrument pastes the therapeutic substance to the diseased site by increasing the pressure of the fluid fed to the opening portions in the vicinity of the diseased site, and thereby separating the therapeutic substance from the sheet support section.

CITATION LIST

Patent Literature

{PTL 1}
Japanese Unexamined Patent Application, Publication No. 2008-173333

SUMMARY OF INVENTION

Technical Problem

In the instrument in Patent Literature 1, the therapeutic substance adheres to the sheet support section at a plurality of positions by the pressure of the fluid fed to the plurality of opening portions from a single pipe line. Therefore, if any of the opening portions is not closed by the therapeutic substance at the time of separation, the fluid leaks from the released one of the opening portions, thereby making it difficult to separate the entire therapeutic substance.

The present invention provides a sheet pasting device which can separate a sheet-shaped substance surely over the entire surface with a simple configuration.

Solution to Problem

One aspect of the present invention provides a sheet pasting device including: an elastically-deformable sheet support section that is provided with a flat surface, and supports a sheet-shaped substance in a state in which the sheet-shaped substance is pasted to the surface; an extrusion member that is provided so as to be able to protrude from and retract into the surface of the sheet support section; and a drive mechanism that causes the extrusion member to protrude from and retract into the surface.

In the above aspect, the sheet support section may include a plurality of holes that open in the surface, and the extrusion member may be a plurality of needle-shaped members whose distal ends are caused to protrude from and retract into the surface at the same time through the two or more holes.

In the above aspect, the needle-shaped members may include, at each of the distal ends, a pointed end portion pierced into the sheet-shaped substance, and a stopper portion arranged on a proximal end side of the pointed end portion and having a larger diameter dimension than the pointed end portion.

In the above aspect, the sheet support section may include a groove that opens in the surface, and the extrusion member may be a wire-shaped member that is accommodated in the groove, and caused to protrude from and retract into the surface.

In the above aspect, the wire-shaped member may be configured in a net-like shape.

Another aspect of the present invention is to provide a sheet pasting device including: an elastically-deformable sheet support section that is provided with a flat surface, and supports a sheet-shaped substance in a state in which the sheet-shaped substance is pasted to the surface with an adhesive; a rod-shaped member that is arranged along the surface of the sheet support section, and is provided movably along the surface in a direction crossing a longitudinal direction of the rod-shaped member; and a drive mechanism that moves the rod-shaped member along the surface.

In the above aspect, the rod-shaped member may include two rod-shaped members, and the drive mechanism may move the two rod-shaped members between a position adjacent to substantially a center of the surface of the sheet support section, and a position apart from each other in the vicinity of an end edge of the surface.

In any of the above aspects, a cylindrical external sheath may be provided, the sheet support section may be provided so as to be able to protrude from and retract into a distal-end opening of the external sheath, and the sheet support section may include an introduction portion having a width dimension decreasing toward a proximal end side, and having a sectional shape curved such that the surface side is located on an inner side.

In any of the above aspects, a convex strip that protrudes radially inward over a predetermined length of a longitudinal direction from an inner surface of a portion of the external sheath where the sheet support section is accommodated may be provided on the inner surface, and the convex strip may include, on at least one side of a circumferential direction, a guide surface that smoothly rises from the inner surface of the external sheath, and directs a widthwise end portion of the accommodated sheet support section radially inward.

DESCRIPTION OF EMBODIMENTS

A sheet pasting device 1 according to a first embodiment of the present invention is described below by reference to the drawings.

For example, the sheet pasting device 1 according to the present embodiment is a device that delivers a sheet-shaped therapeutic substance (substance) A to the vicinity of a diseased site, and pastes the sheet-shaped therapeutic substance A to the diseased site.

As shown in FIGS. 1 to 5, the sheet pasting device 1 includes a sheet support section 2 that supports the sheet-shaped therapeutic substance A in a state in which the sheet-shaped therapeutic substance A is pasted to a surface, an extrusion member 3 (see FIG. 2) that is provided within the sheet support section 2 so as to be able to protrude from and retract into the surface of the sheet support section 2, and a drive mechanism (see FIGS. 4 and 5) 4 that causes the extrusion member 3 to protrude from and retract into the surface.

Figure 1:
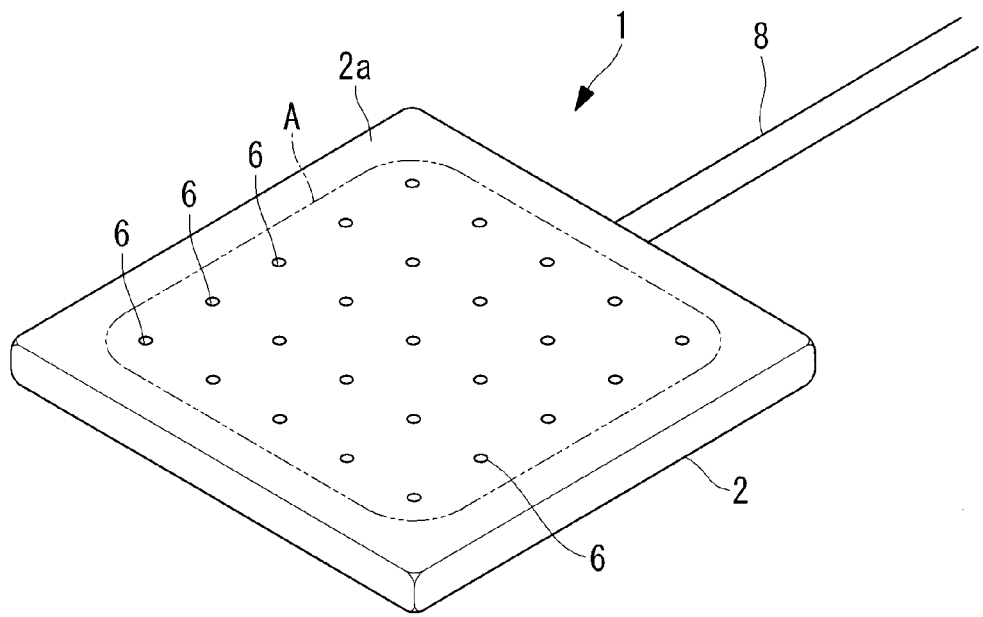
FIG. 1 is a perspective view illustrating a sheet pasting device according to a first embodiment of the present invention.
Figure 3:
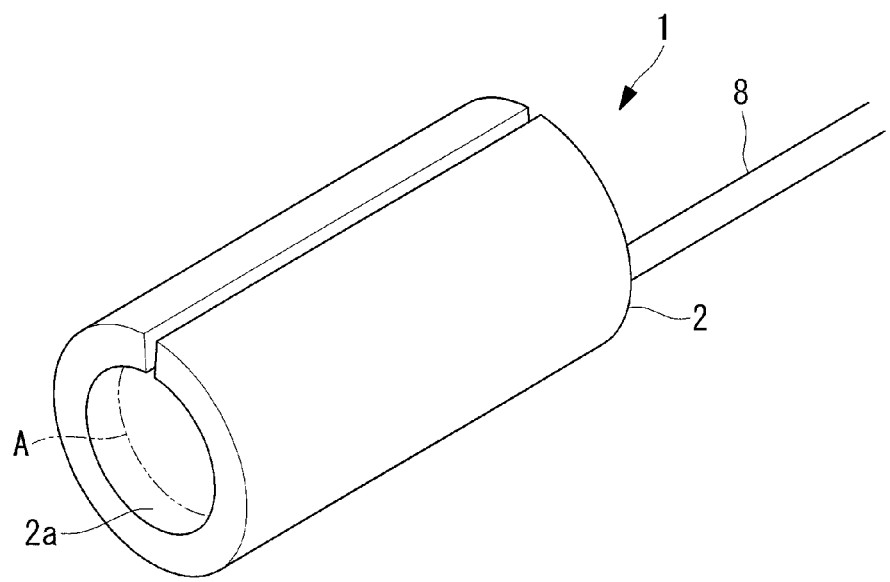
FIG. 3 is a perspective view for explaining the form of a sheet support section when a sheet-shaped substance is delivered by the sheet pasting device in FIG. 1.

The sheet support section 2 is an elastically-deformable member that is formed in a hollow and substantially-rectangular plate-like shape in which a cavity portion 5 is provided, and that can be elastically deformed into a state in which the sheet support section 2 is rolled in a width direction as shown in FIG. 3 by an external force, and can be also deployed into a plate-like shape as shown in FIG. 1 by an elastic restoring force when the external force is released.

A plurality of through holes (holes) 6 that open in a surface 2a of the sheet support section 2 and penetrate into the cavity portion 5 are provided in the surface 2a at intervals from each other.

Figure 2:
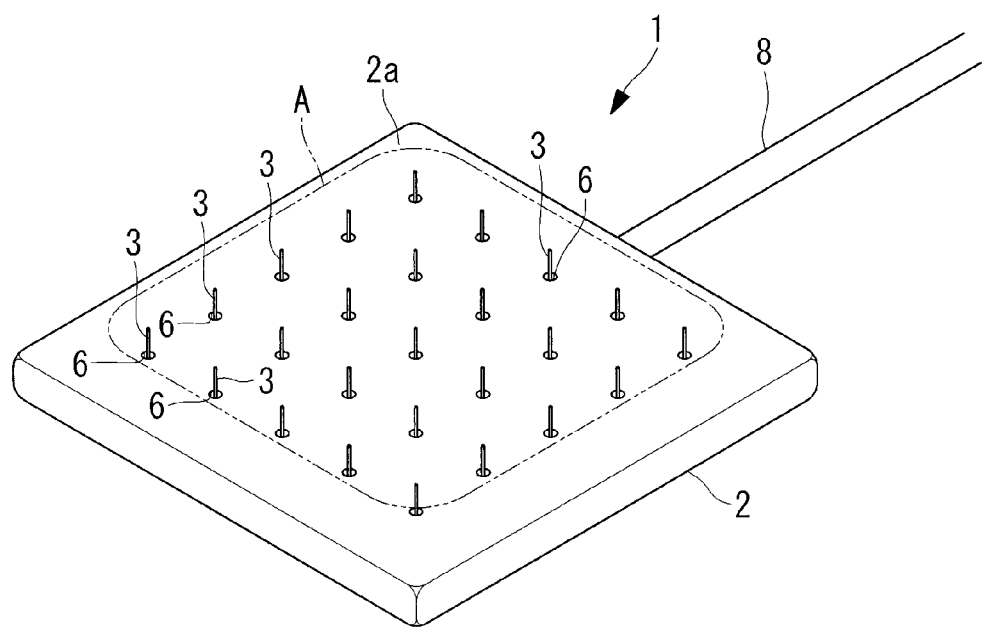
FIG. 2 is a perspective view illustrating a state in which needle-shaped members protrude from openings in a surface of the sheet pasting device in FIG. 1.
Figure 4:
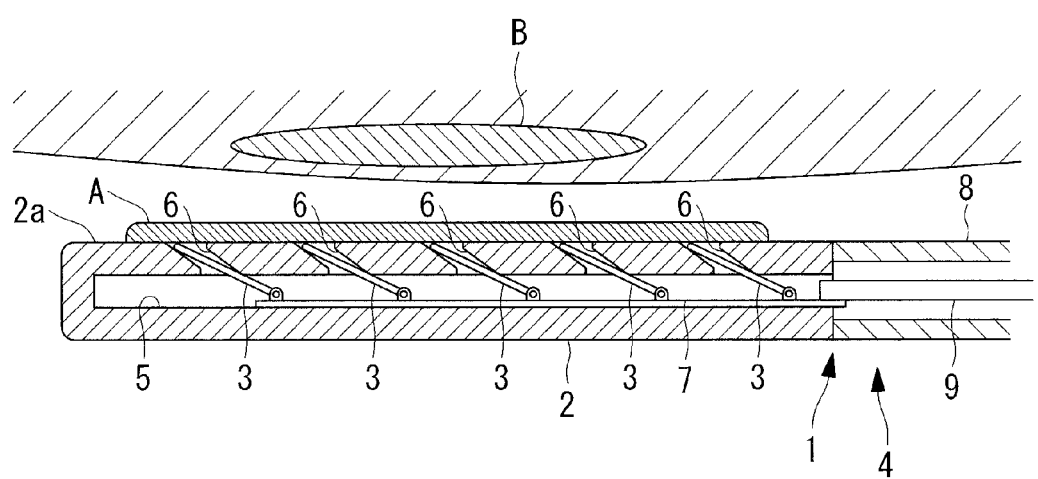
FIG. 4 is a longitudinal sectional view illustrating a state in which the sheet-shaped substance is located close to a target side by the sheet pasting device in FIG. 1.

The extrusion member 3 is composed of a plurality of needle-shaped members (also referred to as needle-shaped members 3 below) that are respectively inserted into the through holes 6 of the sheet support section 2 so as to be movable in a longitudinal direction, and are arranged such that one ends can protrude from and retract into openings of the through holes 6 as shown in FIG. 4. The sheet-shaped therapeutic substance A is pasted to the surface 2a of the sheet support section 2 and delivered in a state in which the needle-shaped members 3 are retracted into the openings of the through holes 6 of the sheet support section 2 as shown in FIG. 1. The needle-shaped members 3 are moved within the through holes 6 to cause the one ends to protrude outside from the openings of the through holes 6 as shown in FIG. 2. Respective portions of the sheet-shaped therapeutic substance A can be thereby pressed by the one ends of the respective needle-shaped members 3, and separated from the surface 2a of the sheet support section 2.

As shown in FIG. 4, the drive mechanism 4 includes an elastically-deformable base member 7 that is accommodated in the cavity portion 5 of the sheet support section 2 so as to be movable forward and backward, and a drive shaft 9 that is inserted into the cavity portion 5 from backward so as to be able to advance and retreat via a hollow shaft 8 coupled to a rear end of the sheet support section 2, and one end of which is coupled to the base member 7.

The other end of each of the needle-shaped members 3 is coupled to the base member 7 within the cavity portion 5 so as to be swingable.

Figure 5:
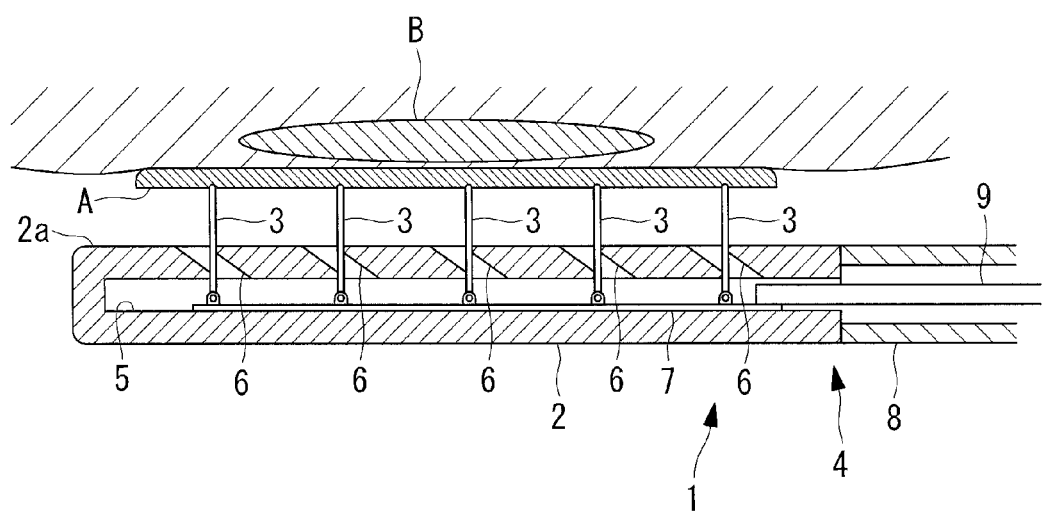
FIG. 5 is a longitudinal sectional view illustrating a state in which the needle-shaped members protrude from the openings in the surface of the sheet pasting device in FIG. 1 so as to paste the sheet-shaped substance to the target site.

Accordingly, as shown in FIG. 4, when the base member 7 is moved backward within the cavity portion 5, all the needle-shaped members 3 are laid down along the base member 7 such that the one ends are arranged inside the through holes 6 so as not to protrude from the openings of the through holes 6. On the other hand, as shown in FIG. 5, when the base member 7 is moved forward within the cavity portion 5, all the needle-shaped members 3 become upright with respect to the base member 7 such that the one ends protrude outside from the openings of the through holes 6.

A case in which the sheet-shaped therapeutic substance A is pasted to a diseased site B by using the sheet pasting device 1 according to the present embodiment having the above configuration is described.

To paste the sheet-shaped therapeutic substance A to the diseased site B by using the sheet pasting device 1 according to the present embodiment, first, the sheet-shaped therapeutic substance A is placed on the surface 2a with all the needle-shaped members 3 retracted into the through holes 6 of the sheet support section 2 by moving the drive shaft 9 backward with respect to the sheet support section 2 as shown in FIGS. 1 to 4.

In this case, the sheet-shaped therapeutic substance A can be placed on the surface 2a of the sheet support section 2 in a bonded state by the viscosity of itself or the surface tension of a liquid such as pure water.

In this state, the sheet-shaped therapeutic substance A and the sheet support section 2 are rolled in the width direction into a cylindrical shape as shown in FIG. 3 by the external force such that the therapeutic substance A is located on the inner side.

Accordingly, the sheet-shaped therapeutic substance A is protected by the sheet support section 2. The maximum width dimension of a cross-sectional surface can be also made smaller. Therefore, the therapeutic substance A can be delivered to the diseased site B through a narrow channel such as a body cavity in an accommodated state in a cylindrical sheath (not shown). At this time, the therapeutic substance A can be protected so as not to come into contact with peripheral tissue.

When the sheet support section 2 is arranged in the vicinity of the diseased site B, the sheet support section 2 is exposed from the sheath, and the external force for holding the sheet support section 2 in a cylindrical shape is released. The sheet support section 2 and the sheet-shaped therapeutic substance A are thereby deployed into a flat form as shown in FIG. 1 by the elastic restoring force of the sheet support section 2.

In this state, the sheet-shaped therapeutic substance A placed on the surface 2a of the sheet support section 2 is moved closer to the diseased site B so as to be opposed to the diseased site B.

The drive shaft 9 is moved forward to advance the base member 7 coupled to the end portion of the drive shaft 9 with respect to the sheet support section 2 as shown in FIGS. 2 to 5. Accordingly, all the needle-shaped members 3 move longitudinally within the corresponding through holes 6, and protrude outside from the openings of the through holes 6. When the base member 7 is pressed to a position in FIG. 5, all the needle-shaped members 3 become upright with respect to the base member 7.

The needle-shaped members 3 protruding from the openings of the through holes 6 press the sheet-shaped therapeutic substance A pasted to the surface 2a of the sheet support section 2 by their distal ends. The needle-shaped members 3 are respectively arranged in the plurality of through holes 6 provided at intervals, and caused to protrude from the openings of the through holes 6 at the same time. Thus, the therapeutic substance A is pressed at a plurality of positions at the same time, and separated from the surface 2a of the sheet support section 2. The sheet-shaped therapeutic substance A is pressed and pasted to the opposed diseased site B.

That is, in accordance with the sheet pasting device 1 according to the present embodiment, since the sheet support section 2 is delivered in a curved state, the sheet-shaped therapeutic substance A can be protected so as not to be damaged during delivery. When the therapeutic substance A is pasted to the diseased site B, the therapeutic substance A is pressed up and separated from the surface 2a of the sheet support section 2 by the plurality of needle-shaped members 3 at the same time. Thus, as compared with a conventional case in which the therapeutic substance is separated by the pressure of a fluid, the separating force is not reduced even after the therapeutic substance A starts to be separated from the surface 2a of the sheet support section 2. Thus, there is an advantage that the therapeutic substance A can be more surely separated and pasted to the diseased site B.

In the present embodiment, the sheet-shaped therapeutic substance A is pressed and separated by the distal ends of the needle-shaped members 3. In this case, the distal ends of the needle-shaped members 3 preferably have a shape difficult to be pierced into the sheet-shaped therapeutic substance A. For example, the distal ends preferably have a flat surface, or a hemispherical surface.

Figure 6A:
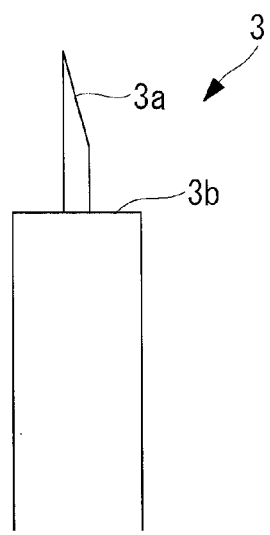
FIG. 6A is an enlarged view illustrating a member including a step portion as a modification of the needle-shaped member of the sheet pasting device in FIG. 1.
Figure 6B:
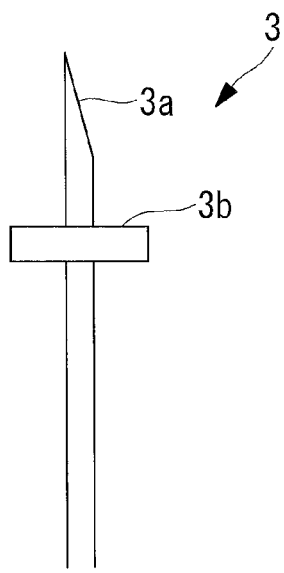
FIG. 6B is an enlarged view illustrating a member including a flange-shaped step portion as a modification of the needle-shaped member of the sheet pasting device in FIG. 1.

Instead, the needle-shaped members 3 may include, at each of the distal ends, a sharply pointed end portion 3a, and a step portion (stopper portion) 3b arranged on the proximal end side of the pointed end portion 3a and having a large diameter dimension as shown in FIG. 6A. The step portion 3b may be also formed in a flange shape as shown in FIG. 6B. In this case, the pointed end portions 3a are preferably arranged so as to protrude outside from the surface 2a of the sheet support section 2 in a state in which the needle-shaped members 3 are retracted deepest into the through holes 6.

Accordingly, a force for holding the therapeutic substance A on the sheet support section 2 can be increased by piercing the pointed end portions 3a of the needle-shaped members 3 into the sheet-shaped therapeutic substance A pasted to the surface 2a of the sheet support section 2. When the therapeutic substance A is pasted to the diseased site B, the step portions 3b arranged on the proximal end side of the pointed end portions 3a and having a large diameter dimension can prevent the needle-shaped members 3 from being further pierced into the therapeutic substance A, and also surely transmit a force for pressing up the therapeutic substance A to the therapeutic substance A.

Figure 7:
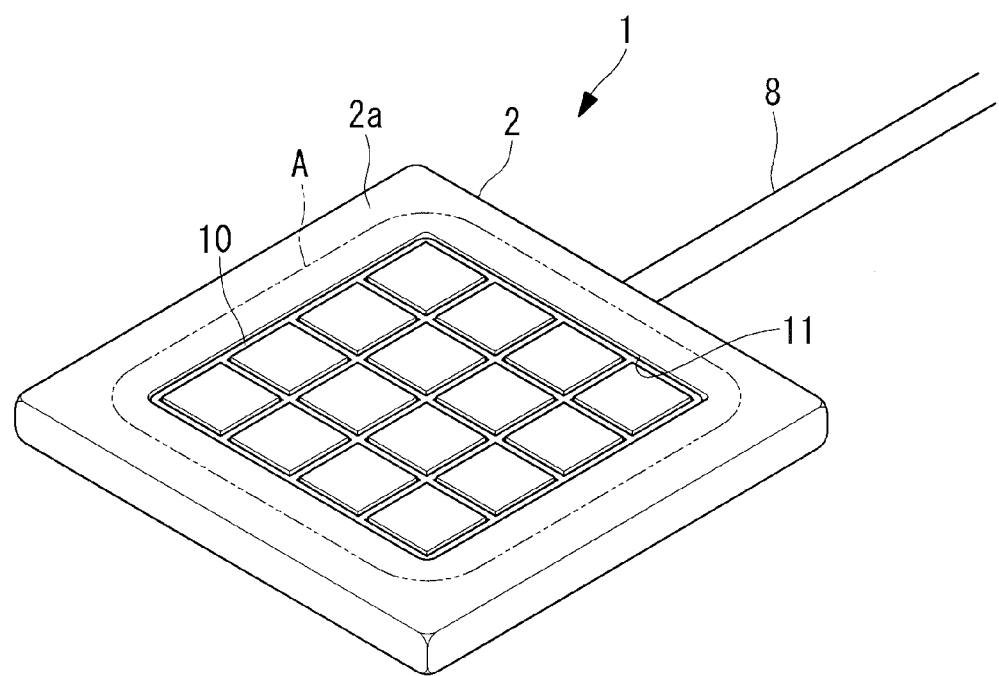
FIG. 7 is a perspective view illustrating a device including an extrusion member composed of a wire member as a modification of the sheet pasting device in FIG. 1.
Figure 8:
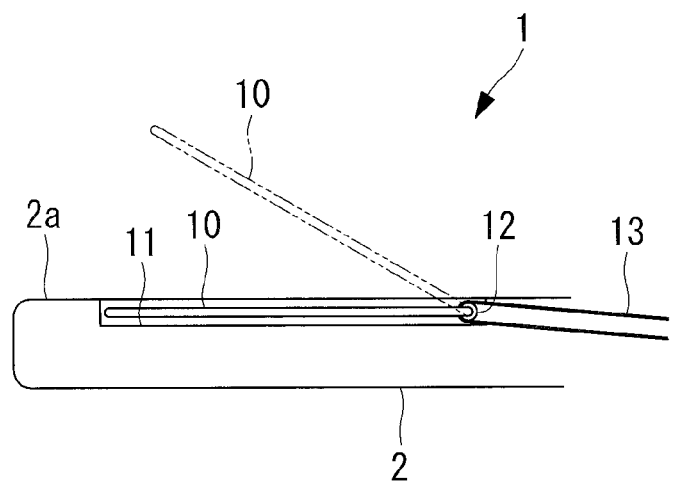
FIG. 8 is a view for explaining the operation of the extrusion member in FIG. 7.

In the present embodiment, the plurality of needle-shaped members 3 are employed as the extrusion member 3. Instead, a wire-shaped member (extrusion member) 10 formed in a net-like shape may be also employed as shown in FIG. 7. In the example shown in FIG. 7, the wire-shaped member 10 is accommodated in a groove 11 formed in the surface 2a of the sheet support section 2. By transmitting a rotating force to a pulley (drive mechanism) 12 attached to one end edge of the wire-shaped member 10 via a belt (drive mechanism) 13 as shown in FIG. 8, the wire-shaped member 10 is caused to protrude from the groove 11 as indicated by a chain line in FIG. 8. The sheet-shaped therapeutic substance A placed on the surface 2a of the sheet support section 2 can be thereby separated from the surface 2a of the sheet support section 2.

At least a portion of the sheet support section 2 is preferably formed of super-elastic alloy so as to obtain a sufficient elastic restoring force.

Next, a sheet pasting device 20 according to a second embodiment of the present invention is described below by reference to the drawings.

In the description of the present embodiment, components common to those of the sheet pasting device 1 according to the first embodiment are assigned the same reference numerals, and the description thereof is omitted.

The sheet pasting device 20 according to the present embodiment includes two rod-shaped members 21 that are arranged on the surface 2a of the sheet support section 2, and are provided movably along the surface 2a in a direction perpendicular to a longitudinal direction of the rod-shaped members 21, and a drive mechanism 22 that moves the rod-shaped members 21 as shown in FIGS. 9 to 12.

In the present embodiment, the sheet support section 2 is also formed of an elastically-deformable material, and the rod-shaped members 21 are also formed of an elastically-deformable material.

A slit-like opening portion 23 that opens linearly in a direction perpendicular to the rod-shaped members 21 is formed in the surface of the sheet support section 2.

Each of the rod-shaped members 21 has a length dimension extending over substantially the entire width of the sheet support section 2. The two rod-shaped members 21 can be moved between a state arranged adjacent to substantially a longitudinal center position of the sheet support section 2, and a state arranged apart from each other at both longitudinal end edges of the sheet support section 2 as shown in FIG. 9.

Figure 11:
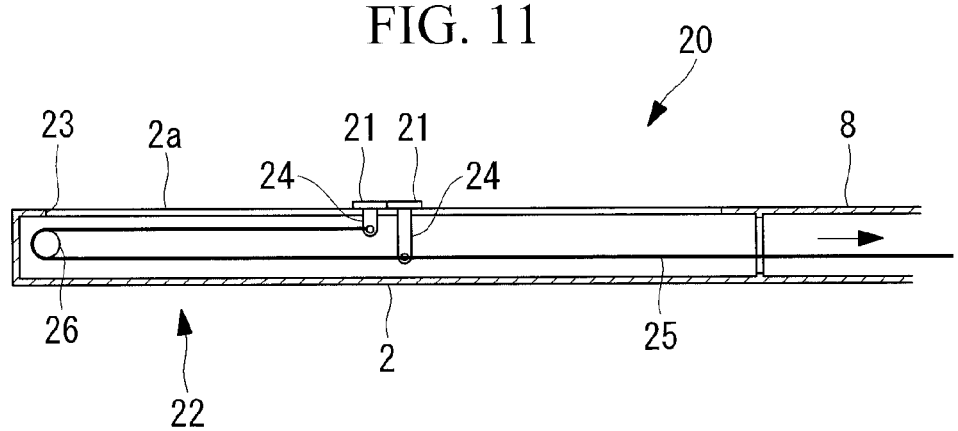
FIG. 11 is a longitudinal sectional view illustrating the sheet pasting device in FIG. 9.
Figure 12:
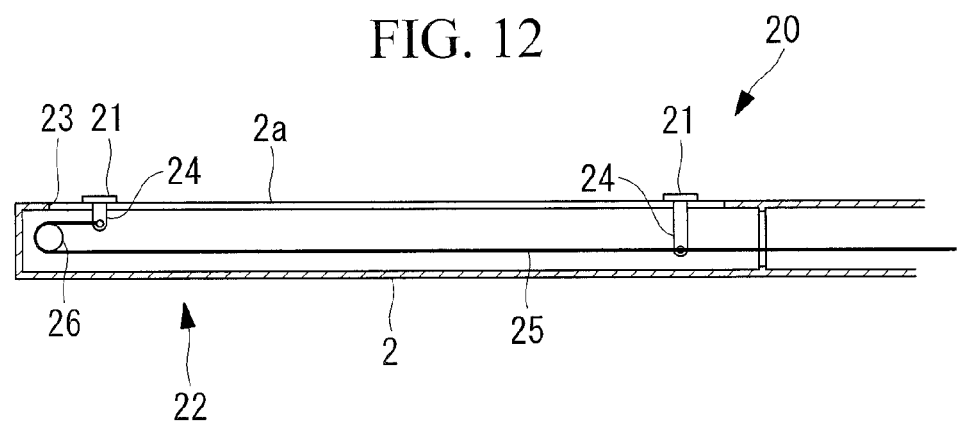
FIG. 12 is a longitudinal sectional view illustrating the sheet pasting device in FIG. 10.

The drive mechanism 22 includes a wire 25 that is connected to a bracket 24 fixed to each of the rod-shaped members 21 and arranged in the cavity portion 5 of the sheet support section 2 via the opening portion 23, and a sheave 26 for holding the wire 25 as shown in FIGS. 11 and 12. The wire 25 is connected to one of the rod-shaped members 21 via the single sheave 26, and an intermediate position of the wire 25 is directly connected to the other of the rod-shaped members 21.

Accordingly, only by pulling the single wire 25 in a direction of an arrow, the two rod-shaped members 21 can be moved at the same time from a state adjacent to each other as shown in FIG. 11 to a state apart from each other as shown in FIG. 12.

Figure 9:
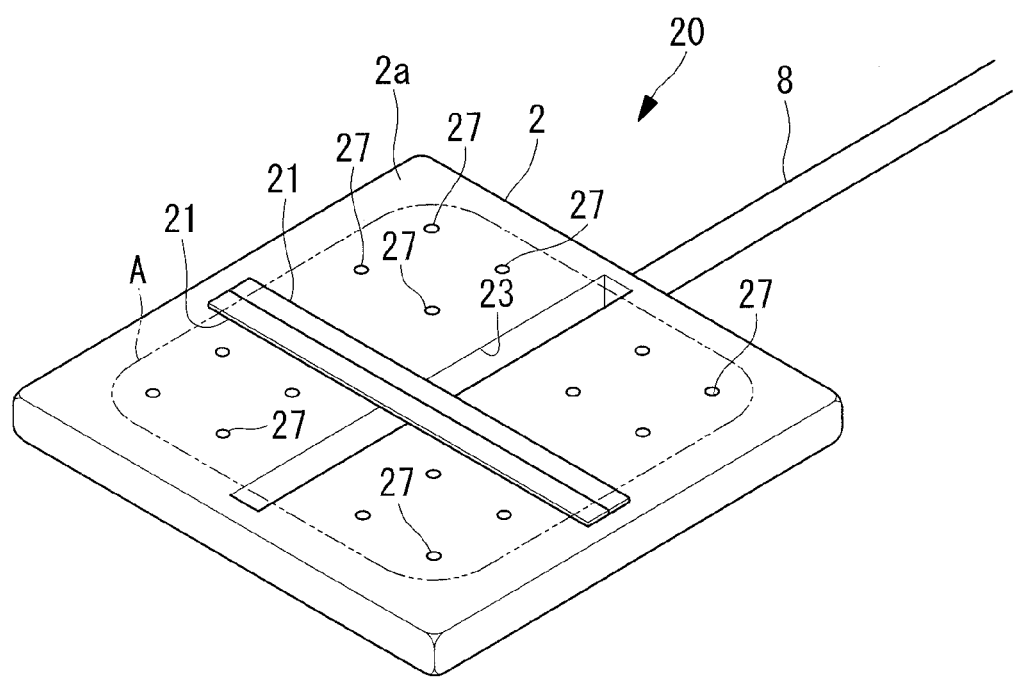
FIG. 9 is a perspective view illustrating a sheet pasting device according to a second embodiment of the present invention.
Figure 10:
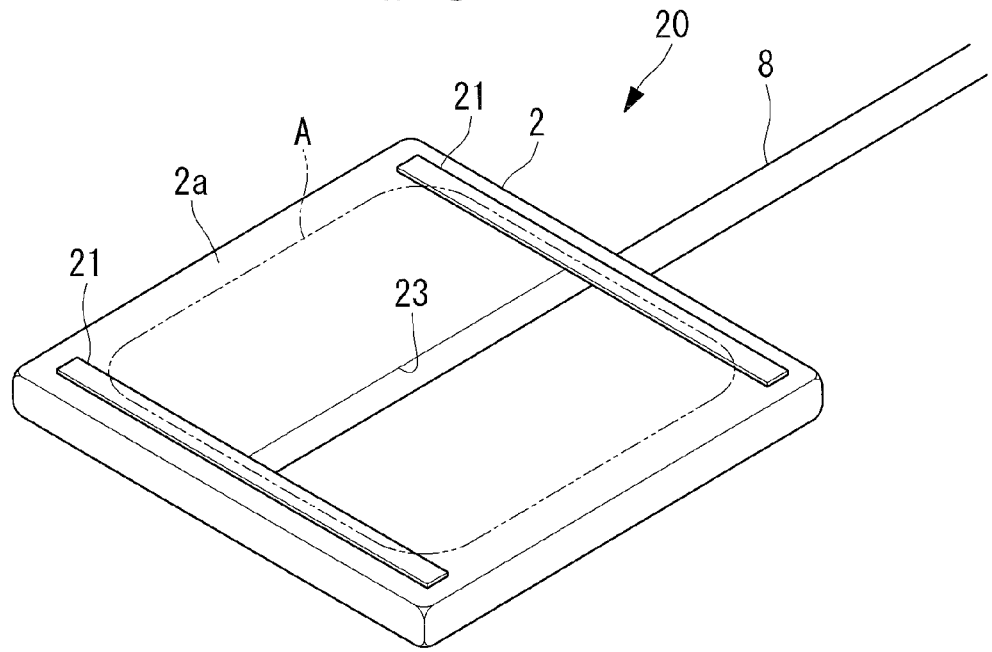
FIG. 10 is a perspective view illustrating a state in which an adhesive force by an adhesive is eliminated by rod-shaped members of the sheet pasting device in FIG. 9.

In FIG. 9, reference numeral 27 denotes an adhesive for bonding the sheet-shaped therapeutic substance A to the surface 2a of the sheet support section 2.

To paste the sheet-shaped therapeutic substance A to the diseased site B by using the sheet pasting device 20 according to the present embodiment having the above configuration, first, the two rod-shaped members 21 are arranged adjacent to substantially the center of the sheet support section 2, and the sheet-shaped therapeutic substance A is bonded to the surface of the sheet support section 2 with the adhesive 27 as shown in FIG. 9. Examples of the adhesive 27 include fibrin glue, gelatin-based adhesive, and sterilized water.

The adhesive 27 may be applied over the entire surface of the sheet-shaped therapeutic substance A, or may be applied to positions existing at intervals as shown in FIG. 9.

The sheet support section 2 on which the sheet-shaped therapeutic substance A is placed as described above can be rolled in a cylindrical shape as shown in FIG. 3, and easily delivered in a form with a small cross-sectional surface while protecting the therapeutic substance A in a similar manner to the first embodiment.

After being delivered to the vicinity of the diseased site B, the sheet support section 2 is deployed such that the sheet-shaped therapeutic substance A placed thereon is opposed to the diseased site B, and the wire 25 is pulled. Accordingly, the pulling force applied to the wire 25 is transmitted to the rod-shaped members 21 via the wire 25 and the sheave 26. The two rod-shaped members 21 are moved in a direction to separate from each other along the surface 2a of the sheet support section 2. As a result, the adhesive 27 for bonding the sheet-shaped therapeutic substance A to the sheet support section 2 is cut off by the rod-shaped members 21, and the adhesive force is eliminated.

Therefore, by pressing the sheet-shaped therapeutic substance A against the diseased site B in this state, the sheet-shaped therapeutic substance A can be easily separated from the sheet support section 2 and pasted to the diseased site B.

In accordance with the sheet pasting device 20 according to the present embodiment, the two rod-shaped members 21 are moved at the same time toward the both ends from substantially the center of the sheet support section 2, so that a stretching force is applied to the sheet-shaped therapeutic substance A in a direction toward the end edges from the center at the same time. As a result, the therapeutic substance A can be advantageously pasted to the diseased site B in a sufficiently stretched state without winkling.

In the present embodiment, the rod-shaped members 21 are also preferably formed of super-elastic alloy.

Figure 13:
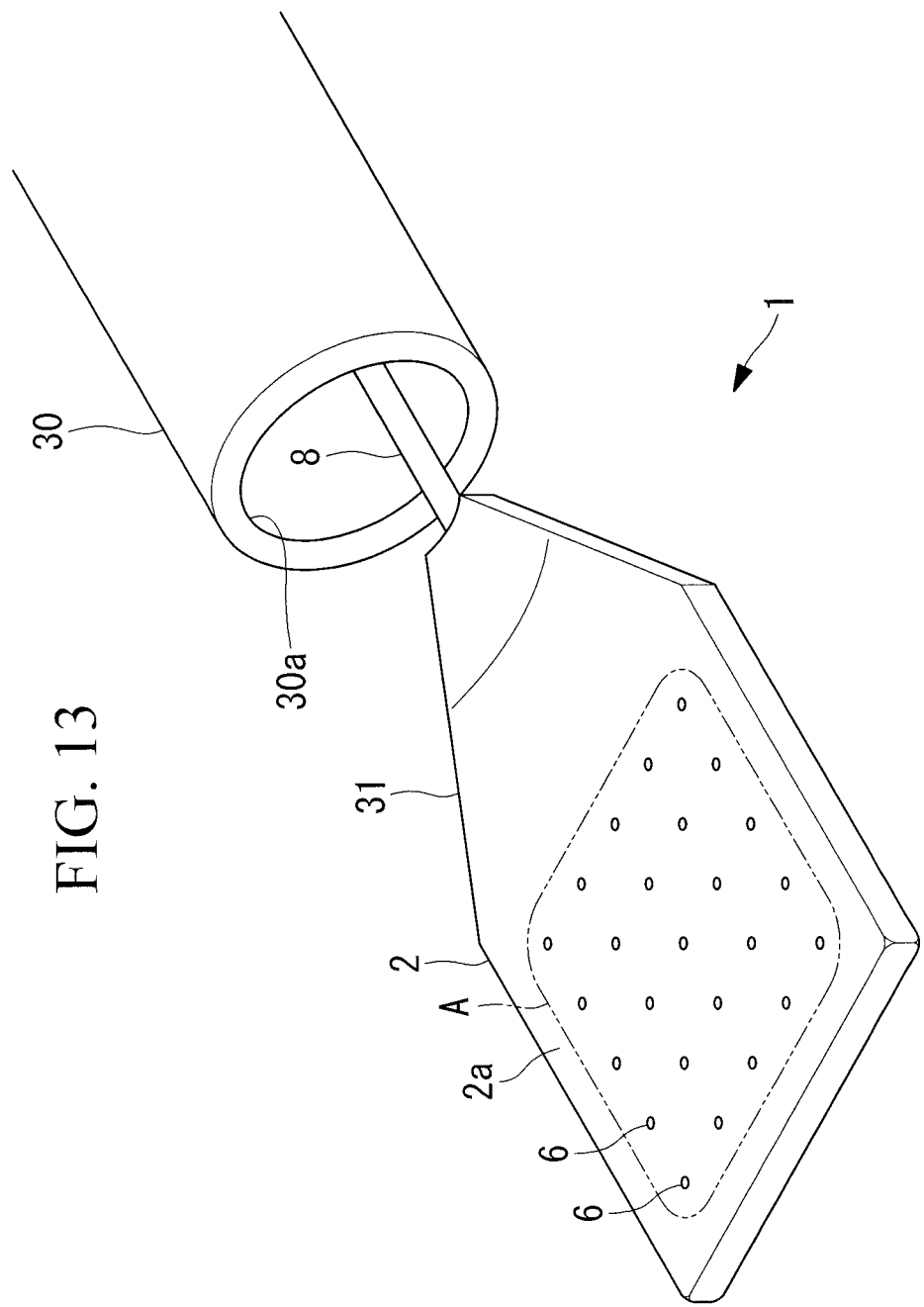
FIG. 13 is a perspective view illustrating a device including an introduction portion at a rear end as a modification of the sheet pasting device in FIG. 1.

In the sheet pasting devices 1 and 20 according to the above respective embodiments, a cylindrical external sheath 30 that accommodates the sheet support section 2 such that the sheet support section 2 can protrude from and retract into a distal-end opening 30a may be also provided. As shown FIG. 13, an introduction portion 31 whose width dimension becomes gradually smaller toward the back is preferably provided on the rear end side of the sheet support section 2. The introduction portion 31 is curved such that the surface 2a of the sheet support section 2 is located on the inner side in its cross sectional shape.

The width dimension of the introduction portion 31 on the backmost side is also formed smaller than the inner diameter dimension of the distal-end opening 30a of the external sheath 30.

Moreover, the width dimension of the sheet support section 2 is formed larger than the inner diameter dimension of the distal-end opening 30a of the external sheath 30. Accordingly, when the sheet support section 2 is pulled into the external sheath 30 from the backmost side of the introduction portion 31, both widthwise end edges of the introduction portion 31 come into contact with an inner edge of the distal-end opening 30a of the external sheath 30 at a lengthwise intermediate position of the introduction portion 31.

When the sheet support section 2 is further pulled into the external sheath 30 from this state, a force toward the widthwise inner side is applied to the introduction portion 31 from the inner edge of the distal-end opening 30a of the external sheath 30. Since the introduction portion 31 is curved such that the surface 2a on which the sheet-shaped therapeutic substance A is placed is located on the inner side, the introduction portion 31 is further curved so as to increase the curvature of the curve when the force toward the widthwise inner side is applied.

Figure 14:
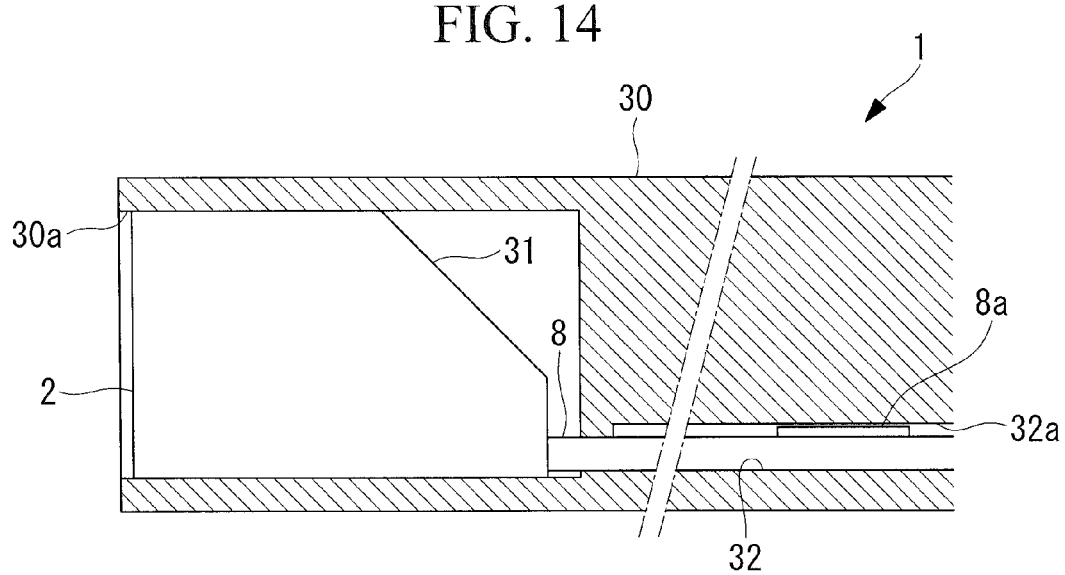
FIG. 14 is a longitudinal sectional view of the sheet pasting device in FIG. 13.

As a result, the sheet support section 2 that is continuous to the introduction portion 31 is also curved in the same direction along with the curving of the introduction portion 31, formed into a cylindrical form as shown in FIG. 3, and pulled into the external sheath 30 as shown in FIG. 14.

That is, after the sheet-shaped therapeutic substance A is pasted to the diseased site B, the sheet support section 2 is rolled in a cylindrical shape and accommodated in the external sheath 30. The sheet support section 2 can be thereby easily delivered out by assuming a compact form similar to that when the sheet-shaped therapeutic substance A is delivered in.

In the present embodiment, rotation of the hollow shaft 8 and the sheet support section 2 fixed to a distal end of the hollow shaft 8 around the axis of the hollow shaft 8 may be restricted by providing a through hole 32 that penetrates through the hollow shaft 8 in the external sheath 30, and fitting together a key groove 32a provided in an inner surface of the through hole 32 and a key 8a provided on an outer surface of the hollow shaft 8 as shown in FIG. 14. Accordingly, the sheet support section 2 and the external sheath 30 are maintained in a given phase, so that it is possible to confirm, on the proximal end side of the external sheath 30, which direction the sheet-shaped therapeutic substance A placed on the surface of the sheet support section 2 is directed.

In this case, the through hole 32 provided in the external sheath 30 is preferably decentered to a position close to an outer surface with respect to the center of the external sheath 30. When the sheet support section 2 is rolled in a cylindrical shape as shown in FIG. 3, the position of the hollow shaft 8 is decentered from the center of the cylindrical sheet support section 2. Thus, by previously decentering the through hole 32, the sheet support section 2 rolled in the cylindrical shape can be easily accommodated in the external sheath 30.

Figure 15:
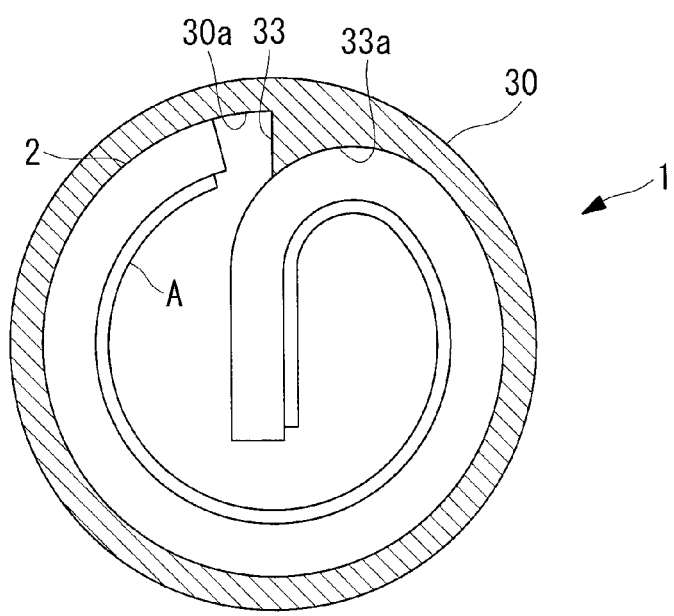
FIG. 15 is a cross sectional view illustrating another modification of the sheet pasting device in FIG. 1.

A convex strip 33 that protrudes radially inward from an inner surface of a portion of the external sheath 30 in which the sheet support section 2 is accommodated may be also provided on the inner surface over a predetermined length of the longitudinal direction as shown in FIG. 15. The convex strip 33 includes a guide surface 33a that smoothly rises from the inner surface of the external sheath 30 on at least one side of a circumferential direction. Accordingly, even when the width dimension of the sheet support section 2 is longer than the peripheral length of the inner surface of the external sheath 30, the sheet support section 2 can be rolled such that a widthwise end portion is directed radially inward by the guide surface 33a, and can be thereby accommodated in the external sheath 30 as shown in FIG. 15. The guide surface 33a may be provided on the both sides of the circumferential direction of the convex strip 33 such that both ends of the sheet support section 2 are directed radially inward.

Also, in the above respective embodiments, the external sheath 30 accommodating the sheet support section 2, the hollow shaft 8, and the drive shaft 9 or the like may have rigidity or flexibility. In a case in which the external sheath 30 or the like are formed of a material having flexibility, even when a channel where the external sheath 30 or the like are introduced (e.g., a channel of a soft outer tube member) is curved, the external sheath 30 or the like can be curved in accordance with the form.

In the above embodiments, the therapeutic substance A is employed as an example of the sheet-shaped substance, and the diseased site B is employed as an example of a target site where the sheet-shaped substance A is to be pasted. Examples of the sheet-shaped therapeutic substance A include a hemostatic agent such as TachoComb (manufactured by CSL Behring), an adhesion barrier such as Seprafilm (manufactured by Kaken Pharmaceutical Co., Ltd.), other adhesives, and a bioabsorbable sheet absorbed in biological tissue.

Next, a pasting jig 40 and a method for pasting the sheet-shaped substance to the sheet support section 2 of the aforementioned sheet pasting devices 1 and 20 are described by reference to the drawings.

Conventionally, there has been a problem that it is necessary for a doctor to cut the therapeutic substance A with scissors and set the cut therapeutic substance A every time the sheet-shaped therapeutic substance A is pasted to the sheet support section 2 of the sheet pasting devices 1 and 20, which is troublesome. To solve the problem, the following solutions are devised.

(Item 1)

A pasting jig including: a cutting section that is provided adjacent to a surface of a sheet support section, and can cut a sheet-shaped substance into an area equal to or smaller than that of the surface between the pasting jig and the sheet support section, and a positioning section that performs positioning between the cutting section and the sheet support section.

Figure 16:
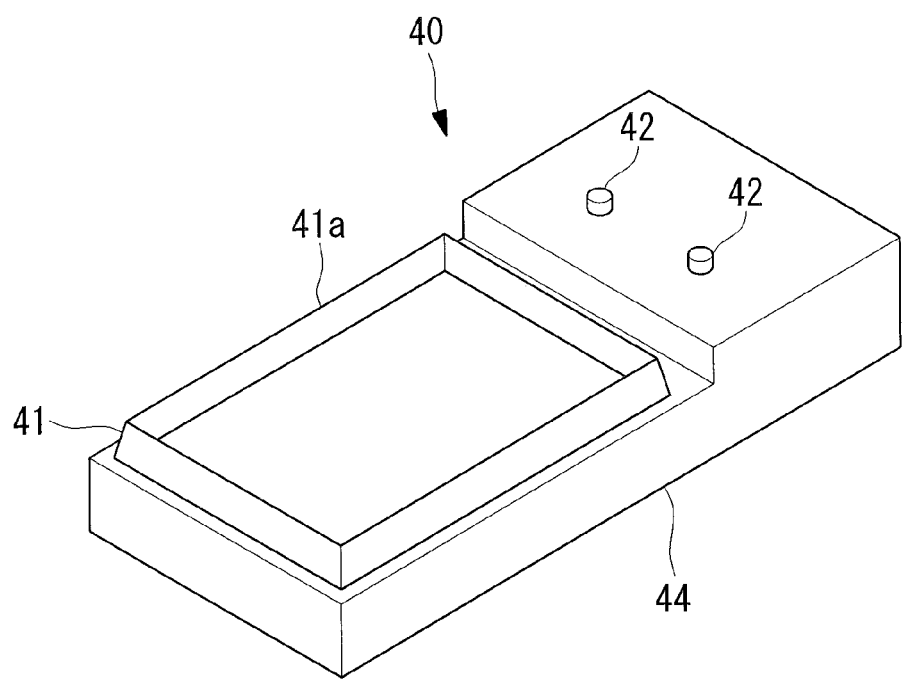
FIG. 16 is a perspective view illustrating a pasting device for pasting a sheet-shaped substance to a sheet pasting device.
Figure 17:
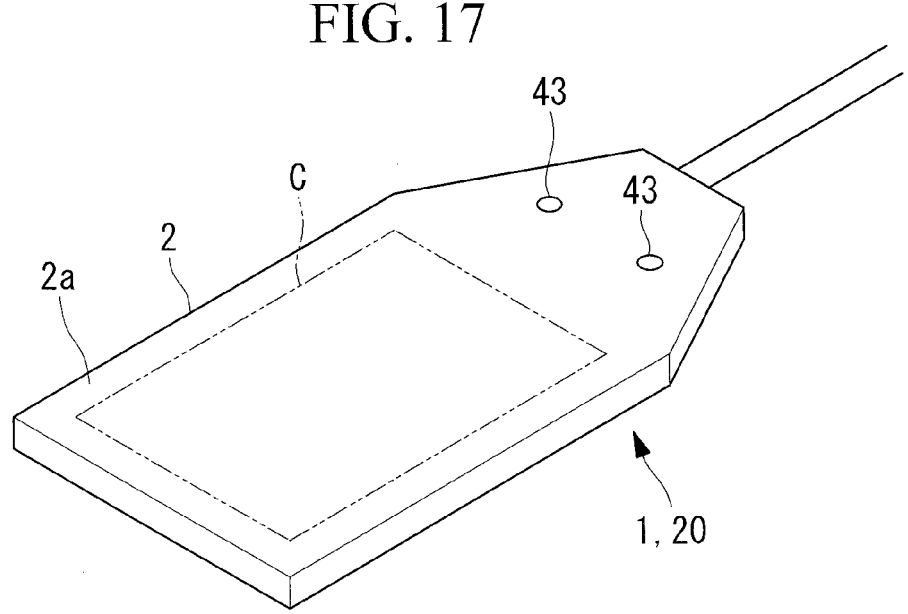
FIG. 17 is a perspective view illustrating a sheet pasting device to which the pasting device in FIG. 16 can be attached in a positioned state.

As shown in FIG. 16, the pasting jig 40 includes a rectangular cutting section 41 having a smaller area than the surface of the sheet support section 2 (see FIG. 17), and a protrusion (positioning section) 42 that positions the cutting section 41 with respect to the sheet support section 2. On the other hand, as shown in FIG. 17, a concave portion (positioning section) 43 to which the protrusion 42 is fitted is provided in the sheet support section 2.

A surface where the protrusion 42 of the pasting jig 40 is provided is set at substantially the same height position as a cutting edge 41a of the cutting section 41. The concave portion 43 of the sheet support section 2 is arranged flush with the surface 2a on which the sheet-shaped substance A is placed. That is, when the protrusion 42 of the pasting jig 40 is fitted to the concave portion 43 of the sheet support section 2, the cutting section 41 is arranged at a position (a position indicated by a chain line C in FIG. 17) where the cutting edge 41a contacts the surface 2a of the sheet support section 2.

In accordance with the pasting jig 40, a sheet-shaped substance larger than the sheet-shaped substance A to be pasted is arranged on the surface 2a of the sheet support section 2, and the sheet-shaped substance A is cut off by the cutting section 41 between the pasting jig 40 and the sheet support section 2 in a state in which the cutting section 41 and the sheet support section 2 are positioned by the protrusion 42 and the concave portion 43. Accordingly, the sheet-shaped substance A having an area equal to or smaller than the surface 2a of the sheet support section 2 can be pasted to the surface 2a of the sheet support section 2 in a positioned state. That is, cutting of the sheet-shaped substance A and pasting to the sheet support section 2 can be advantageously performed in one step.

(Item 2)

The pasting jig according to the item 1, wherein the cutting section is fixed to a plate-like member that can cover the entire surface of the sheet support section.

The pasting jig 40 includes a plate-like member 44 that covers the entire cutting section 41 as shown in FIGS. 16 to 18. Accordingly, the sheet-shaped substance A is arranged on the surface 2a of the sheet support section 2 with the surface 2a directed vertically upward, and the pasting jig 40 is moved closer from vertically above to cut the sheet-shaped substance A by the cutting section 41. In the cutting operation, the upper side of the sheet-shaped substance A is covered with the plate-like member 44. Consequently, dust or the like falling from above during the operation can be prevented from adhering to the sheet-shaped substance A.

In the example shown in FIGS. 16 and 17, the cutting section 41 and the sheet support section 2 are positioned by fitting the protrusion 42 to the concave portion 43. It is also possible to employ the pasting jig 40 including a bracket 45 that is arranged in position on the sheet support section 2, the plate-like member 44 that is urged vertically upward with respect to the bracket 45 by a spring 46, and the cutting section 41 that is downwardly fixed to a lower portion of the plate-like member 44 as shown in FIGS. 18A and 18B.

Accordingly, by positioning the sheet support section 2 in a lower portion of the bracket 45, and moving down the plate-like member 44 against the urging force of the spring 46 in a state in which the sheet-shaped substance A larger than the surface 2a of the sheet support section 2 is arranged on the surface 2a, the sheet-shaped substance A can be cut off by the downward cutting section 41, and pasted to the entire surface 2a of the sheet support section 2.

Figure 18A:
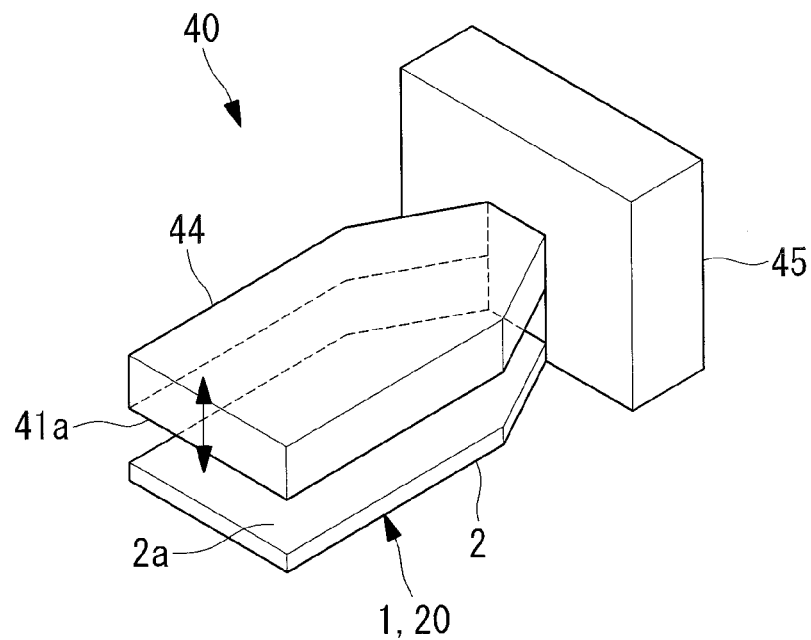
FIG. 18A is a perspective view illustrating a modification of the pasting device in FIG. 16.
Figure 18B:
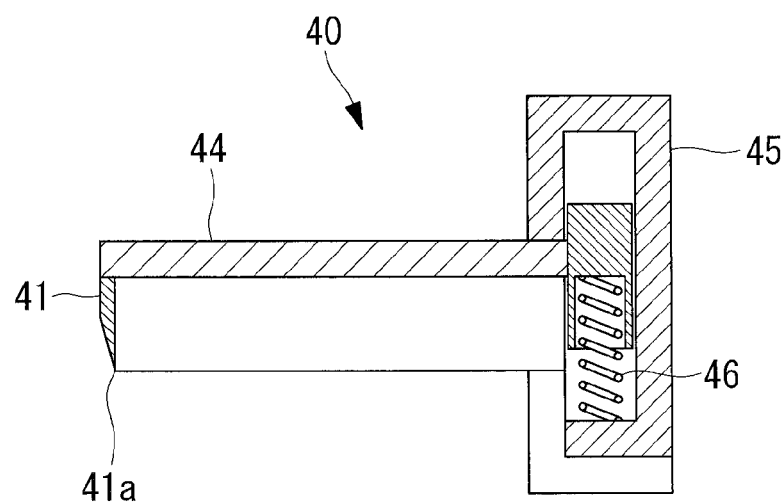
FIG. 18B is a longitudinal sectional view illustrating the modification of the pasting device in FIG. 16.

In the example shown in FIGS. 18A and 18B, the cutting section 41 has the same shape as the outer shape of the sheet support section 2, and the cutting section 41 is moved down along an outer edge of the sheet support section 2 outside the outer edge, so that the sheet-shaped substance A can be easily cut off by shearing.

(Item 3)

The pasting jig according to the item 1 or 2, including a pressing section that is made of an elastic material elastically deformable between a position protruding from a cutting edge of the cutting section and a position retracted from the cutting edge.

(Item 4)

The pasting jig according to the item 3, including a restricting member that is arranged at a position retracted from the cutting edge of the cutting section, and restricts further elastic deformation of the pressing section.

Figure 19:
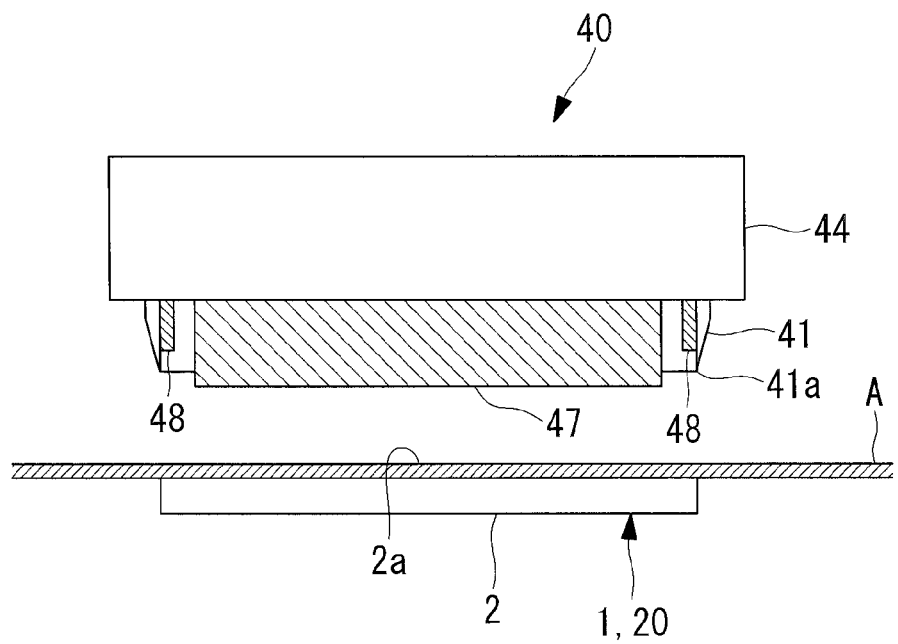
FIG. 19 is a view illustrating a state before the sheet-shaped substance is cut off as a modification of the pasting device in FIG. 16.
Figure 20:
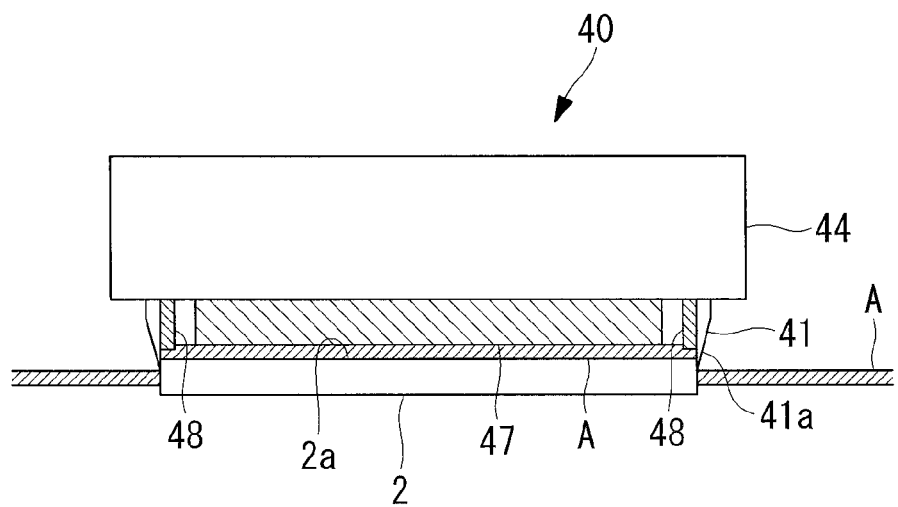
FIG. 20 is a view illustrating a state after the sheet-shaped substance is cut off by the pasting device in FIG. 19.

As shown in FIGS. 19 and 20, the pasting jig 40 includes a pressing section 47 that is made of an elastic material such as rubber and sponge on the inner side of the rectangular cutting section 41 as shown in FIG. 16. The pressing section 47 protrudes to the distal end side from the cutting section 41 as shown in FIG. 19 at a stage before the cutting section 41 comes into contact with the sheet-shaped substance A. The pressing section 47 can be elastically deformed to a position retracted to the proximal end side from the cutting section 41 as shown in FIG. 20 at a stage of cutting the sheet-shaped substance A.

Also, a restricting member 48 that is arranged at a position retracted from the cutting edge 41a of the cutting section 41, and comes into abutment against the sheet-shaped substance A at a point of time when the pressing section 47 is compressed, thereby restricting further compression of the pressing section 47 is provided at a position adjacent to the inner side of the cutting section 41.

Accordingly, the pressing section 47 is in contact with the sheet-shaped substance A before the cutting section 41 cuts the sheet-shaped substance A, and keeps pressing the sheet-shaped substance A even during cutting. Thus, there is an advantage that the cutting operation can be stably performed.

By providing the restricting member 48, pressing of the sheet-shaped substance A with an excessive force by the pressing section 47 is suppressed. Even when the sheet-shaped substance A is soft, the soundness can be maintained.

Figure 21:
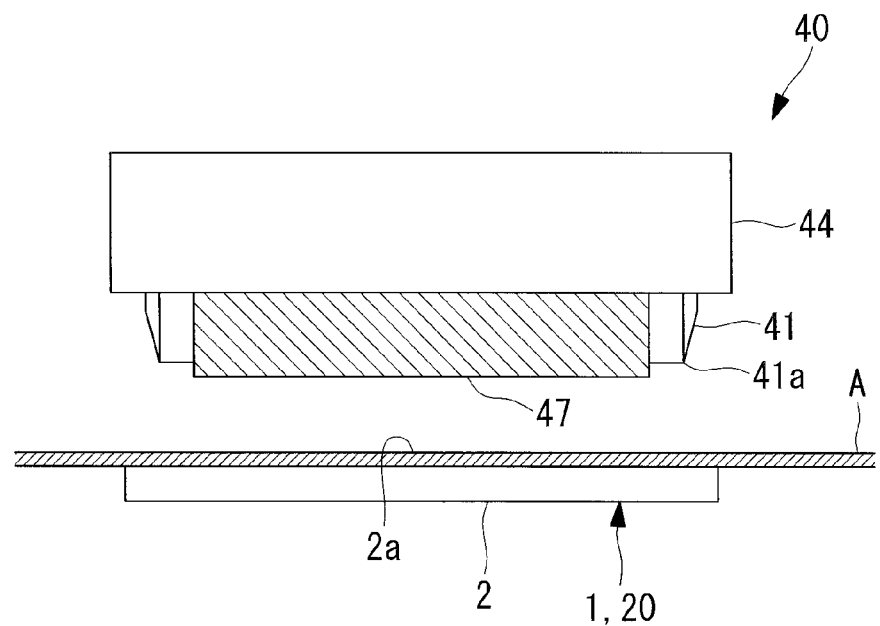
FIG. 21 is a view illustrating a state before the sheet-shaped substance is cut off as another modification of the pasting device in FIG. 16.
Figure 22:
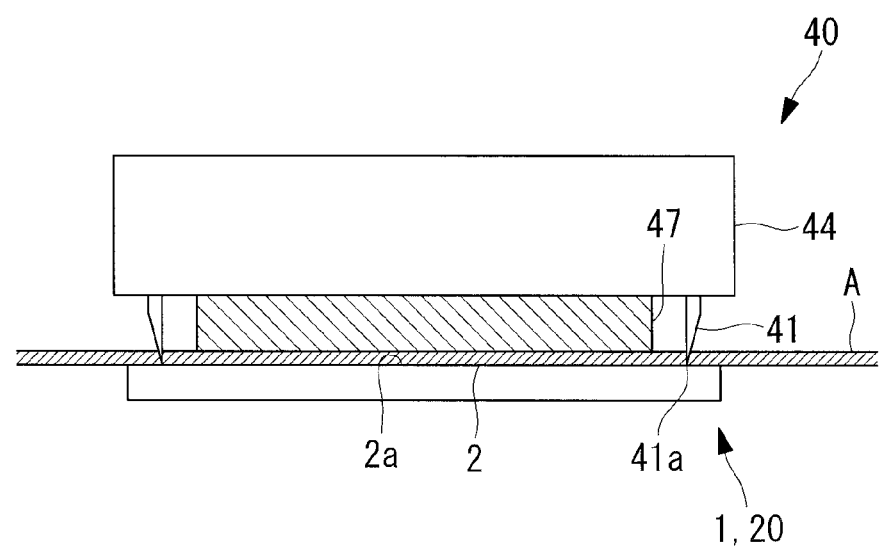
FIG. 22 is a view illustrating a state after the sheet-shaped substance is cut off by the pasting device in FIG. 21.

When the sheet-shaped substance A is cut off by bringing the cutting edge 41a of the cutting section 41 into abutment against the surface 2a of the sheet support section 2 as shown in FIGS. 21 and 22, the cutting section 41 itself serves as a restricting member, so that it is not necessary to separately provide the restricting member.

The method for pasting the sheet-shaped substance A by using the above pasting jig 40 is as follows.

(Item 5)

A method for pasting a sheet-shaped substance by using the pasting jig according to any of the items 1 to 4, including:

an arranging step of arranging the sheet-shaped substance on the surface of the sheet support section;

a positioning step of positioning the sheet support section and the pasting jig; and a cutting step of cutting the sheet-shaped substance by the cutting section of the pasting jig.

(Item 6)

The method for pasting a sheet-shaped substance according to the item 5, wherein the cutting step is performed while covering the upper side of the sheet-shaped substance arranged on the surface of the sheet support section.

(Item 7)

The method for pasting a sheet-shaped substance according to the item 5 or 6, wherein the cutting step is performed while pressing the sheet-shaped substance arranged on the surface of the sheet support section against the sheet support section throughout cutting from before cutting.

The following aspects can be derived from the embodiment described above.

One aspect of the present invention provides a sheet pasting device including: an elastically-deformable sheet support section that is provided with a flat surface, and supports a sheet-shaped substance in a state in which the sheet-shaped substance is pasted to the surface; an extrusion member that is provided so as to be able to protrude from and retract into the surface of the sheet support section; and a drive mechanism that causes the extrusion member to protrude from and retract into the surface.

In accordance with the present invention, by pasting the sheet-shaped substance to the surface of the sheet support section, and curving the sheet support section such that the surface on the sheet-shaped substance side is located on the inner side, the sheet-shaped substance can be delivered while being protected. When the sheet-shaped substance is pasted to a target site, the sheet support section is deployed such that the sheet-shaped substance is opposed to the target site, and the drive mechanism is operated to cause the extrusion member to protrude from the surface of the sheet support section. Accordingly, the sheet-shaped substance pasted to the surface of the sheet support section can be pressed by the extrusion member, separated from the surface of the sheet support section, and pasted to the target site.

In this case, in accordance with the present aspect, the separating force is not weakened even after the sheet-shaped substance starts to be separated from the surface of the sheet support section unlike in a conventional case in which the sheet-shaped substance is separated by the pressure of a fluid discharged from a plurality of opening portions. Thus, the sheet-shaped substance can be separated surely over the entire surface with a simple configuration.

In the above aspect, the sheet support section may include a plurality of holes that open in the surface, and the extrusion member may be a plurality of needle-shaped members whose distal ends are caused to protrude from and retract into the surface at the same time through the two or more holes.

Accordingly, when the drive mechanism is operated, the needle-shaped members are respectively caused to protrude from the plurality of holes opening in the surface of the sheet support section. The sheet-shaped substance can be thereby pressed by the needle-shaped members at the two or more positions, and separated from the sheet support section easily and more surely over the entire surface.

In the above aspect, the needle-shaped members may include, at each of the distal ends, a pointed end portion pierced into the sheet-shaped substance, and a stopper portion arranged on a proximal end side of the pointed end portion and having a larger diameter dimension than the pointed end portion.

Accordingly, when the sheet-shaped substance is supported on the sheet support section with the needle-shaped members slightly protruding from the surface of the sheet support section, the pointed end portions provided at the distal ends of the needle-shaped members are pierced into the sheet-shaped substance, so that the sheet-shaped substance can be supported so as not to fall off the sheet support section.

In this case, by abutting against the stopper portions provided on the proximal end side of the pointed end portions, the sheet-shaped substance is held such that the needle-shaped members are not pierced any more. When the drive mechanism is operated, the sheet-shaped substance can be pressed by the stopper portions, separated from the sheet support section, and easily pasted to the target site.

In the above aspect, the sheet support section may include a groove that opens in the surface, and the extrusion member may be a wire-shaped member that is accommodated in the groove, and caused to protrude from and retract into the surface.

Accordingly, when the drive mechanism is operated, the wire-shaped member is caused to protrude from the groove opening in the surface of the sheet support section. The sheet-shaped substance can be thereby pressed by a line by the wire-shaped member, and separated from the sheet support section easily and more surely over the entire surface.

In the above aspect, the wire-shaped member may be configured in a net-like shape.

Accordingly, the sheet-shaped substance can be pressed at more positions by the net-like wire-shaped member. It is thereby possible to separate the sheet-shaped substance from the sheet support section more surely over the entire surface while dispersing the pressing force applied to the sheet-shaped substance.

Another aspect of the present invention is to provide a sheet pasting device including: an elastically-deformable sheet support section that is provided with a flat surface, and supports a sheet-shaped substance in a state in which the sheet-shaped substance is pasted to the surface with an adhesive; a rod-shaped member that is arranged along the surface of the sheet support section, and is provided movably along the surface in a direction crossing a longitudinal direction of the rod-shaped member; and a drive mechanism that moves the rod-shaped member along the surface.

Accordingly, by pasting the sheet-shaped substance to the surface of the sheet support section with an adhesive, and curving the sheet support section such that the surface on the sheet-shaped substance side is located on the inner side, the sheet-shaped substance can be delivered while being protected. When the sheet-shaped substance is pasted to a target site, the sheet support section is deployed such that the sheet-shaped substance is opposed to the target site, and the drive mechanism is operated to move the rod-shaped member, which is arranged along the surface of the sheet support section, along the surface of the sheet support section in the direction crossing the longitudinal direction. Adhesion between the sheet-shaped substance and the sheet support section with the adhesive can be thereby cut off, so that the sheet-shaped substance can be separated from the surface of the sheet support section, and pasted to the target site.

In the above aspect, the rod-shaped member may include two rod-shaped members, and the drive mechanism may move the two rod-shaped members between a position adjacent to substantially a center of the surface of the sheet support section, and a position apart from each other in the vicinity of an end edge of the surface.

Accordingly, the sheet-shaped substance is bonded to the sheet support section with the adhesive in a state in which the rod-shaped members are arranged adjacent to substantially the center of the surface of the sheet support section. When the sheet-shaped substance is pasted to the target site, the two rod-shaped members are spaced apart from each other, and moved to the vicinity of end portions of the surface of the sheet support section. The adhesion over the entire surface of the sheet-shaped substance can be thereby cut off by the rod-shaped members. In this case, a force applied to the sheet-shaped substance from the rod-shaped members can be equally distributed in two directions. The sheet-shaped substance can be thereby prevented from wrinkling.

In any of the above aspects, a cylindrical external sheath may be provided, the sheet support section may be provided so as to be able to protrude from and retract into a distal-end opening of the external sheath, and the sheet support section may include an introduction portion having a width dimension decreasing toward a proximal end side, and having a sectional shape curved such that the surface side is located on an inner side.

Accordingly, the sheet support section where the sheet-shaped substance is pasted to the surface can be accommodated in the cylindrical external sheath and delivered in a state in which the sheet support section is rolled in a width direction, so that the sheet-shaped substance is protected so as not to come into contact with a peripheral object during delivery. When the sheet support section is caused to protrude from the distal-end opening of the external sheath after being delivered to the target site, the sheet support section is deployed by its elastic restoring force, thereby exposing the sheet-shaped substance pasted to the surface. Consequently, the sheet-shaped substance can be easily pasted to the target site.

In this case, after the sheet-shaped substance is pasted, the sheet support section is moved in a direction into the external sheath. The introduction portion provided on the proximal end side of the sheet support section has a width dimension decreasing toward the proximal end side. Thus, when the introduction portion is pulled into the distal-end opening of the external sheath, widthwise end edges of the introduction portion come into contact with an inner edge of the distal-end opening of the external sheath on the way, and the introduction thereby receives an external force toward the widthwise inner side from the inner edge.

Since the introduction portion has a sectional shape curved such that the surface side is located on the inner side, the external force acts as a force for curving the sheet support section such that the surface is located on the inner side. Thus, the sheet support section can be rolled in the width direction and easily accommodated in the external sheath. Accordingly, when the sheet support section is moved after pasting the sheet-shaped substance, the sheet support section can be also moved in a rolled compact state without interfering with the periphery.

In any of the above aspects, a convex strip that protrudes radially inward over a predetermined length of a longitudinal direction from an inner surface of a portion of the external sheath where the sheet support section is accommodated may be provided on the inner surface, and the convex strip may include, on at least one side of a circumferential direction, a guide surface that smoothly rises from the inner surface of the external sheath, and directs a widthwise end portion of the accommodated sheet support section radially inward.

Accordingly, when the sheet support section is accommodated in the external sheath while being rolled in the width direction, a portion of the sheet support section climbs onto the convex strip, so that the widthwise end portion is directed radially inward away from the inner peripheral surface of the external sheath. As a result, even when the width dimension of the sheet support section is larger than the inner peripheral length of the external sheath, the sheet support section can be accommodated in the external sheath by partially overlapping the widthwise end portions.

Advantageous Effects of Invention

The present invention provides an effect that the sheet-shaped substance can be separated surely over the entire surface with a simple configuration.

The invention claimed is:

1. A sheet pasting device comprising:
    an elastically-deformable sheet support section that is provided with a flat surface, and supports a sheet-shaped substance in a state in which the sheet-shaped substance is pasted to the surface;
    an extrusion member that is provided so as to be able to protrude from and retract into the surface of the sheet support section;
    a drive mechanism that causes the extrusion member to protrude from and retract into the surface; and
    a cylindrical external sheath that accommodates the sheet support section where the sheet-shaped substance is pasted to the surface in a state in which the sheet support section is rolled in a width direction.

2. The sheet pasting device according to claim 1,
    wherein the sheet support section includes a plurality of holes that open in the surface, and
    the extrusion member is a plurality of needle-shaped members whose distal ends are caused to protrude from and retract into the surface at the same time through the two or more holes.

3. The sheet pasting device according to claim 2,
    wherein the needle-shaped members include, at each of the distal ends, a pointed end portion pierced into the sheet-shaped substance, and a stopper portion arranged on a proximal end side of the pointed end portion and having a larger diameter dimension than the pointed end portion.

4. The sheet pasting device according to claim 1,
    wherein the sheet support section includes a groove that opens in the surface, and
    the extrusion member is a wire-shaped member that is accommodated in the groove, and caused to protrude from and retract into the surface.

5. The sheet pasting device according to claim 4,
    wherein the wire-shaped member is configured in a net-like shape.

6. A sheet pasting device comprising:
    an elastically-deformable sheet support section that is provided with a flat surface, and supports a sheet-shaped substance in a state in which the sheet-shaped substance is pasted to the surface with an adhesive;
    a rod-shaped member that is arranged along the surface of the sheet support section, and is provided movably along the surface in a direction crossing a longitudinal direction of the rod-shaped member; and
    a drive mechanism that moves the rod-shaped member along the surface.

7. The sheet pasting device according to claim 6,
    wherein the rod-shaped member includes two rod-shaped members, and
    the drive mechanism moves the two rod-shaped members between a position adjacent to substantially a center of the surface of the sheet support section, and a position apart from each other in the vicinity of an end edge of the surface.

8. The sheet pasting device according to claim 1,
    wherein the sheet support section is provided so as to be able to protrude from and retract into a distal-end opening of the external sheath, and
    the sheet support section includes an introduction portion having a width dimension decreasing toward a proximal end side, and having a sectional shape curved such that the surface side is located on an inner side.

9. The sheet pasting device according to claims 6,
    wherein a cylindrical external sheath is provided,
    the sheet support section is provided so as to be able to protrude from and retract into a distal-end opening of the external sheath, and
    the sheet support section includes an introduction portion having a width dimension decreasing toward a proximal end side, and having a sectional shape curved such that the surface side is located on an inner side.

10. The sheet pasting device according to claim 8,
    wherein a convex strip that protrudes radially inward over a predetermined length of a longitudinal direction from an inner surface of a portion of the external sheath where the sheet support section is accommodated is provided on the inner surface, and
    the convex strip includes, on at least one side of a circumferential direction, a guide surface that smoothly rises from the inner surface of the external sheath, and directs a widthwise end portion of the accommodated sheet support section radially inward.

11. The sheet pasting device according to claim 9,
    wherein a convex strip that protrudes radially inward over a predetermined length of a longitudinal direction from an inner surface of a portion of the external sheath where the sheet support section is accommodated is provided on the inner surface, and the convex strip includes, on at least one side of a circumferential direction, a guide surface that smoothly rises from the inner surface of the external sheath, and directs a widthwise end portion of the accommodated sheet support section radially inward.

* * * * *